(12) United States Patent
Sarachan et al.

(10) Patent No.: US 9,613,254 B1
(45) Date of Patent: Apr. 4, 2017

(54) QUANTITATIVE IN SITU CHARACTERIZATION OF HETEROGENEITY IN BIOLOGICAL SAMPLES

(71) Applicant: GENERAL ELECTRIC COMPANY, Schenectady, NY (US)

(72) Inventors: Brion Daryl Sarachan, Schenectady, NY (US); John Frederick Graf, Ballston Lake, NY (US); Vidya Pundalik Kamath, Greenville, SC (US)

(73) Assignee: General Electric Company, Niskayuna, NY (US)

( * ) Notice: Subject to any disclaimer, the term of this patent is extended or adjusted under 35 U.S.C. 154(b) by 28 days.

(21) Appl. No.: 14/871,667

(22) Filed: Sep. 30, 2015

(51) Int. Cl.
   *G06K 9/00* (2006.01)
   *G06K 9/62* (2006.01)
   *G06K 9/32* (2006.01)

(52) U.S. Cl.
   CPC ....... *G06K 9/00147* (2013.01); *G06K 9/0014* (2013.01); *G06K 9/00134* (2013.01); *G06K 9/3241* (2013.01); *G06K 9/6215* (2013.01); *G06K 9/6219* (2013.01); *G06K 9/6224* (2013.01)

(58) Field of Classification Search
   USPC ....................................................... 382/133
   See application file for complete search history.

(56) References Cited

U.S. PATENT DOCUMENTS

| 7,761,240 B2 | 7/2010 | Saidi et al. |
| 8,488,863 B2 | 7/2013 | Boucheron |
| 8,948,474 B2 | 2/2015 | Chang et al. |
| 2003/0049626 A1* | 3/2003 | Jendoubi ............. C12Q 1/6809 435/6.16 |
| 2010/0177950 A1 | 7/2010 | Donovan et al. |
| 2013/0051650 A1* | 2/2013 | Santamaria-Pang .... G06F 19/24 382/133 |
| 2013/0060775 A1 | 3/2013 | Qiu et al. |
| 2013/0084570 A1 | 4/2013 | Hatzis et al. |

(Continued)

FOREIGN PATENT DOCUMENTS

| WO | 2013106116 A1 | 7/2013 |
| WO | 2014055635 A1 | 4/2014 |
| WO | 2014102130 A1 | 7/2014 |

OTHER PUBLICATIONS

Zhou et al., "A hybrid algorithm of minimum spanning tree and nearest neighbor for classifying human cancers", Advanced Computer Theory and Engineering (ICACTE), 2010 3rd International Conference on . . . , Aug. 20-22, 2010, vol. 5 pp. V5-585-V5-589 Conference Location: Chengdu.*

(Continued)

*Primary Examiner* — Gregory F Cunningham
(74) *Attorney, Agent, or Firm* — Eileen B. Gallagher

(57) ABSTRACT

The present disclosure relates to characterization of biological samples. By way of example, a biological sample may be contacted with a plurality of probes specific for targets in the sample, such as probes for immune markers and segmenting probes. Acquired image data of the sample may be used to segment the images into epithelial and stromal regions to characterize individual cells in the sample based on the binding of the probes. Further, the biological sample may be characterized by a heterogeneity of the characterized cells.

22 Claims, 14 Drawing Sheets

(56) References Cited

U.S. PATENT DOCUMENTS

| | | | |
|---|---|---|---|
| 2013/0122513 A1* | 5/2013 | Petersson | B03C 1/288 435/7.1 |
| 2013/0230230 A1 | 9/2013 | Ajemba et al. | |
| 2013/0287790 A1 | 10/2013 | Hsu et al. | |

OTHER PUBLICATIONS

Sood et al., "Multiplexing technology for in situ biomarker profiling of Non-Small Cell Lung Cancer (NSCLC)", Dec. 2014, Multiomyx.

* cited by examiner

| F | F | H | H | E | E | C |
|---|---|---|---|---|---|---|
| H | C | C | C | H | H | C |
| H | F | B | C | H | F | B |
| C | F | E | H | G | B | A |
| A | F | F | C | C | A | F |
| F | C | B | F | F | B | E |
| A | H | E | B | C | C | F |

FIG. 13

QUANTITATIVE IN SITU CHARACTERIZATION OF HETEROGENEITY IN BIOLOGICAL SAMPLES

BACKGROUND

The subject matter disclosed herein relates to cell profiling of biological samples. More particularly, the disclosed subject matter relates to determining one or more cell characteristics of the biological sample, including a distribution, type, heterogeneity, and/or location of cells within the sample.

Various methods may be used in biology and in medicine to observe different targets in a biological sample. For example, analysis of proteins in histological sections and other cytological preparations may be performed using the techniques of histochemistry, immunohistochemistry (IHC), or immunofluorescence.

Many of the current techniques may detect a presence or concentration of biological targets, e.g., biomarkers, without maintaining information about original location of those targets within the sample. For example, certain techniques involve processing the sample in such a way that the original location information is lost. Other techniques may involve assessing only a limited number of targets from a given sample Further analysis of targets may require additional sampling from the source (e.g., a repeated biopsy), thereby limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis. However, spatial distribution of biomarker expression or other features within a sample may be clinically informative.

BRIEF DESCRIPTION

In one embodiment, a method for determining heterogeneity of cell populations in a biological sample is provided. The method includes receiving image data of a biological sample comprising a plurality of cells, wherein the image data is representative of expression of a plurality of biomarkers; segmenting the plurality of cells into individual cells in the biological sample based on the image data; quantitating cell features of the individual cells in the biological sample based on the image data; generating a plurality of cell types for the individual cells, wherein each respective cell type is based on a set of cell characteristics, wherein the cell characteristics comprise a common set of biomarker expression levels, cell features, or a combination thereof; assigning the individual cells to only one of the generated cell types; determining a molecular heterogeneity value of the biological sample based on the assigning; determining a spatial heterogeneity value of the biological sample based at least on one individual cell assigned to an individual cell type and a physical distance to other cells of the same cell type or cell type heterogeneity within a predetermined physical distance of the at least one individual cell; and determining a heterogeneity metric based on the molecular heterogeneity value and the spatial heterogeneity value.

In another embodiment, a method for determining heterogeneity of cell populations in a biological sample is provided. The system includes receiving image data from a biological sample; selecting a plurality of biomarker characteristics of interest, wherein the biomarker characteristics comprise one or more predetermined expression levels of respective biomarkers; determining a number of cell types in the biological sample based on the plurality of biomarker characteristics; assigning individual cells in the biological sample to only one of the determined cell types; calculating a physical distance across the biological sample between a plurality of cells assigned to the same cell type; and outputting a heterogeneity metric based on the number of cell types and the calculated physical distance.

In another embodiment, an image acquisition device configured to acquire image data from a biological sample is provided. The device includes a memory storing instructions that, when executed, results in: receiving image data of a biological sample comprising a plurality of cells, wherein the image data is representative of expression of a plurality of biomarkers; segmenting the plurality of cells into individual cells in the biological sample based on the image data; quantitating morphological features of the individual cells in the image data; generating a plurality of cells types for the individual cells, wherein each respective cell type is based on a set of cell characteristics, wherein the cell characteristics comprise a common set of biomarker expression levels and morphological features; assigning the individual cells to only one of the generated cell types; determining a molecular heterogeneity value of the biological sample based on the assigning; determining a spatial heterogeneity of the biological sample based at least on one individual cell assigned to an individual cell type and a physical distance to other cells of the same cell type or a cell type heterogeneity within a predetermined physical distance of the at least one individual cell; and a processor configured to execute the instructions stored in the memory; and a graphical user interface configured to display at least a portion of the image data and the heterogeneity metric output.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 13 shows classification of cells based on pathway states depending on protein expression;

DETAILED DESCRIPTION

Tumors demonstrate a significant amount of intra-tumor heterogeneity in terms of observable features including tissue morphology, physiology and histology, gene expression, genotype, metastatic, angiogenic and proliferative potential. Some indications of heterogeneity include characteristics such as size, morphology and protein expression and behaviors like cell turnover, cell-cell interaction, invasive and metastatic ability and sensitivity to pharmacologic interventions. Cell heterogeneity may be linked to clinical outcomes. For example, an increase in heterogeneity may be linked to cancer progression.

The present disclosure relates to a technique for in situ, multiplexed sub-cellular analysis of tissue sample data to assess heterogeneity. Cell-level and subcellular-level protein expressions may be quantified using image analysis algorithms, and the results may be used to determine heterogeneity of the sample. For example, analysis of these protein expression measurements in conjunction with morphological features of cells and their spatial location may be employed to measure the heterogeneity that may be observed in a tissue sample.

In one embodiment, a diversity index or other heterogeneity metric may be generated. For example, the diversity index may be expressed in two parts: the molecular heterogeneity observed in the sample due to differences in protein expression and cellular morphology; and spatial (or social) heterogeneity observed in the sample due to spatial dispersion of cells. The interpretation of these measures may be performed in conjunction with a biological context of the sample, such as tumor grade, tumor prognosis etc. and may also be interpreted in different ways. For example, higher tumor heterogeneity might be associated with poorer outcome for stage II patients but better patient outcome for late tumor stages. A calibration plot for tissue heterogeneity may be provided. In one embodiment, ground truth measurements may be used to convert such calibration plots into calibration curves that can directly provide meaningful biological context to the diversity index.

Figure 1:
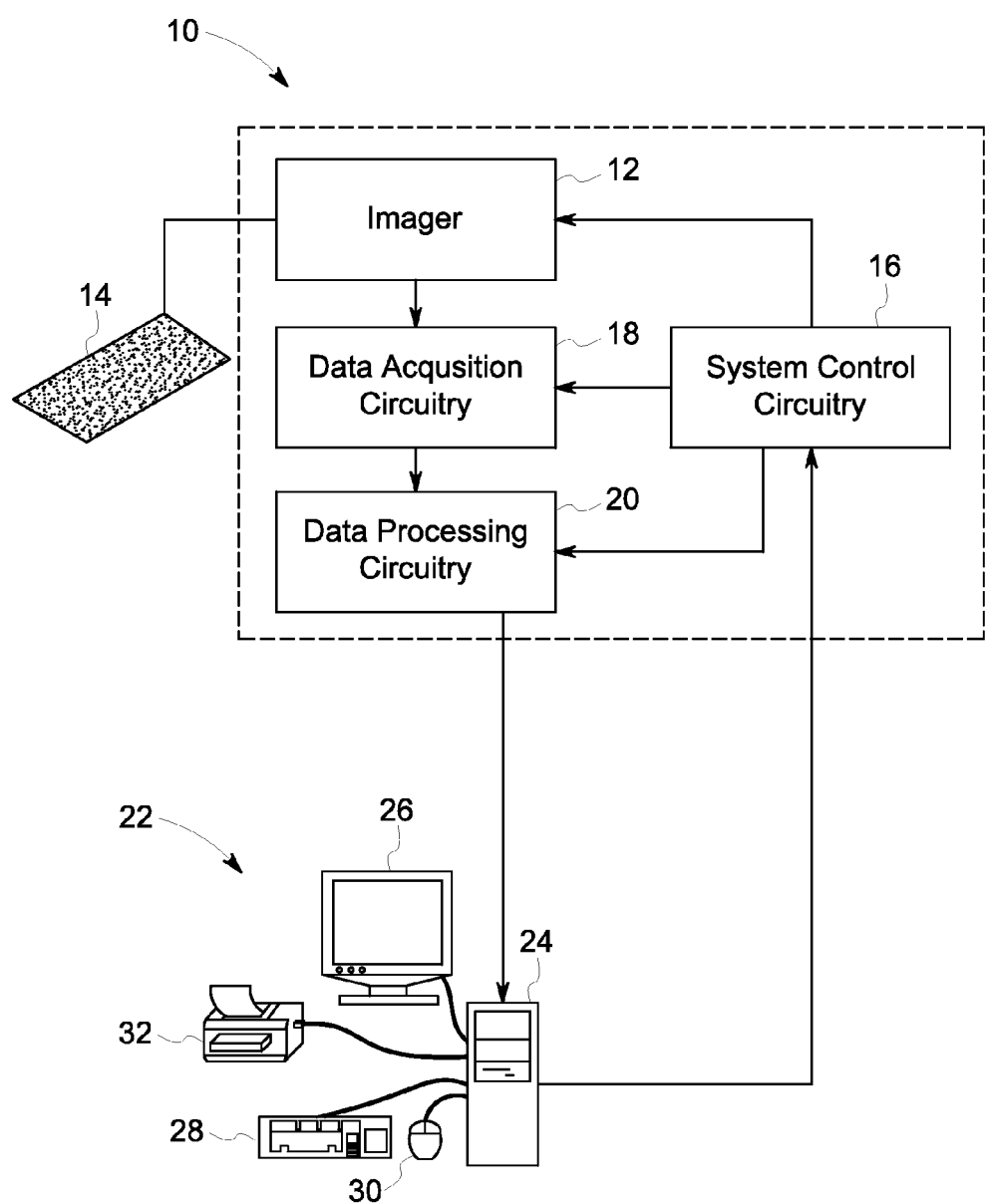
FIG. 1 is a block diagram illustrating an embodiment of a system for assessing a biological sample according to an embodiment of the present disclosure.

The present techniques provide systems and methods for image analysis. In certain embodiments, it is envisioned that the present techniques may be used in conjunction with previously acquired images, for example, digitally stored images, in retrospective studies. In other embodiments, the images may be acquired from a physical sample. In such embodiments, the present techniques may be used in conjunction with an image acquisition system. An exemplary imaging system 10 capable of operating in accordance with the present technique is depicted in FIG. 1. Generally, the imaging system 10 includes an imager 12 that detects signals and converts the signals to data that may be processed by downstream processors. The imager 12 may operate in accordance with various physical principles for creating the image data and may include a fluorescent microscope, a bright field microscope, or devices adapted for suitable imaging modalities. In general, however, the imager 12 creates image data indicative of a biological sample including a population of cells 14, shown here as being multiple samples on a tissue micro array, either in a conventional medium, such as photographic film, or in a digital medium. As used herein, the term "biological material" or "biological sample" refers to material obtained from, or located in, a biological subject, including biological tissue or fluid obtained from a subject. Such samples may be, but are not limited to, body fluid (e.g., blood, blood plasma, serum, or urine), organs, tissues, biopsies, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, an antigen from a biological fluid (e.g., blood or urine). The biological samples may be imaged as part of a slide.

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic, electronic, or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquisition image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple wells of a multi-well plate). The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the computer 24 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the computer 24. The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images. Thus, the image processing, segmenting, and/or enhancement techniques described herein may be carried out remotely from the imaging system, as on completely separate and independent workstations that access the image data, either raw, processed or partially processed and perform the steps and functions described herein to improve the image output or to provide additional types of outputs (e.g., raw data, intensity values, cell profiles).

Further, it should be understood that the disclosed outputs may also be provided via the system 10. For example, the system 10 may generate metrics or values based on the disclosed techniques and may display or provide other indications of such values via the system 10. In one embodiment, the displayed outputs may include plots or images representative of molecular and/or spatial heterogeneity (e.g., minimum spanning trees). In another embodiment, the displayed outputs may include pathway state maps. Based on the outputs, a caregiver may make diagnosis and/or treatment decisions. For example, based on molecular and/or spatial heterogeneity, a caregiver may make determinations as to appropriate drug treatments.

As provided herein, the present techniques may be applied to multiplexed image data to yield one or more metrics of sample heterogeneity of a biological sample. For example, molecular heterogeneity may be assessed to determine a number of different clonal types within a sample. A higher molecular heterogeneity of a tumor may correlate with higher drug resistance and recurrence potential. The techniques may incorporate univariate approaches to detect inflections in the histograms of biomarker expression. In addition, multivariate approaches consider all the cells in feature space, perhaps with dimensionality reduction, to detect widely separate "islands" of cells. Other approaches may include standard deviation/skewness/kurtosis for features, unsupervised clustering, etc. In addition, the present techniques assess spatial heterogeneity to assess how cells are different from their neighbors. A higher spatial heterogeneity may correlate with metastatic potential and recurrence. In one approach, a spanning tree among similar cells in Euclidian space is used extract metrics on the lengths of the line segments. The metrics may in turn be used to determine a spatial heterogeneity value or metric. The molecular and spatial heterogeneity may be combined to determine an overall or combined heterogeneity metric.

Figure 2:
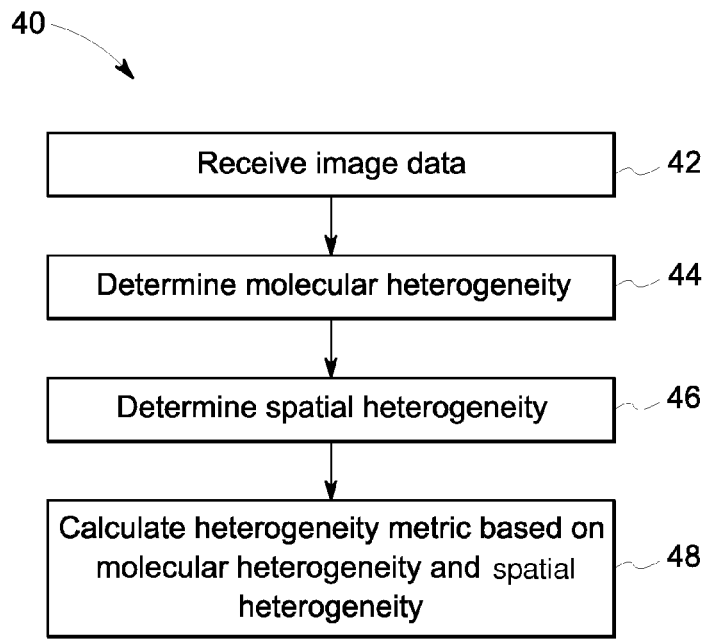
FIG. 2 is a flow diagram of a quantitative in situ characterization of heterogeneity according to an embodiment of the present disclosure.

FIG. 2 is a flow diagram of one embodiment of a technique 40 determining an overall heterogeneity metric as provided herein. At step 42, image data is received by imaging system 10. The image data may be gathered by a multi-molecular, multiplexing imaging technology such as the GE Healthcare MultiOmyx™ platform. The technique 40 then continues to step 44 and determines a molecular heterogeneity value. The molecular heterogeneity value is calculated by the data processing circuitry 20 and is based on the number of different cell types present or cell diversity in the biological sample 14. Cells that belong to the same type (or exhibit a similar molecular signature) will still differ from each other to a degree that is smaller than the difference between distinct types. Proceeding to step 46, the data processing circuitry 20 then determines a spatial heterogeneity value. The spatial heterogeneity value is a measure of how different cells in the biological sample 14 are compared to their neighbors. In one embodiment of the method, the spatial heterogeneity value may be calculated based on the molecular heterogeneity value. At step 48, a diversity index, is calculated based on the molecular heterogeneity value and the spatial heterogeneity value as calculated by step 44 and 46 respectively. Examples of heterogeneity calculation techniques may include variance in an image feature; unsupervised techniques such as clustering or Principal Component Analysis; supervised techniques such as machine learning algorithms and combinations of these.

Figure 3:
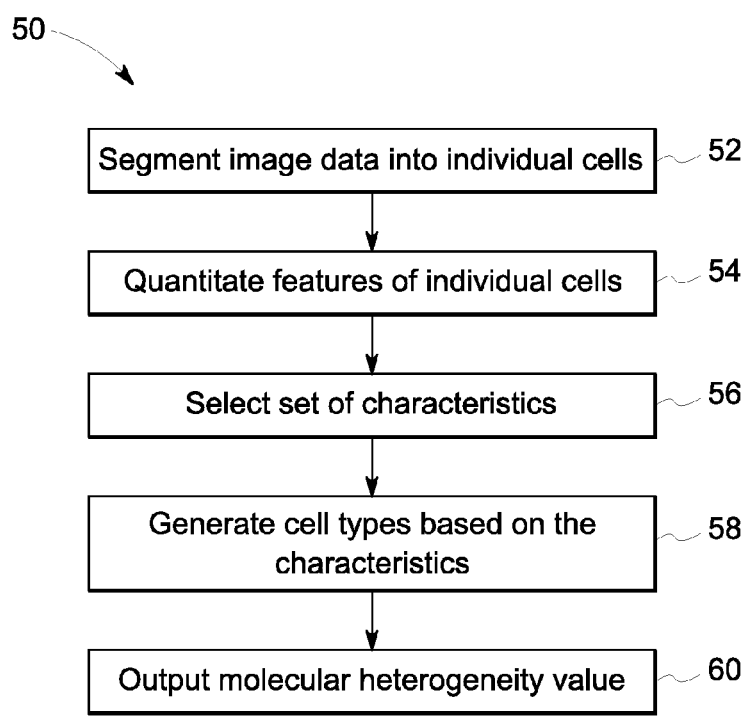
FIG. 3 is a flow diagram of a molecular heterogeneity characterization according to an embodiment of the present disclosure.

FIG. 3 is a technique 50 for determining molecular heterogeneity values or indexes of image data. In certain techniques, image analysis algorithms may be used to delineate single cells and sub-cellular components (nucleus, cytoplasm and membrane) using structural protein markers in tissue sections at step 52. Then features of individual cells are determined at step 54. Features available for measuring heterogeneity within compartments include protein expression values within single cells and/or sub-cellular components of the cells as well as morphological characteristics such as area of the cell, eccentricity and other such shape descriptors. Heterogeneity may be determined by computing basic moments in the data at a univariate level, such as standard deviation of the underlying data distribution (square root of the variance). Higher level moments such as skewness and kurtosis, when used in combination with the lower moments (mean and variance of the underlying data distribution), tends to provide a reliable indicators of groups in the data. For example, a positive value of skewness signifies a distribution with an asymmetric tail extending out towards more positive x; a negative value signifies a distribution whose tail extends out towards more negative x; Kurtosis measures the relative peakedness or flatness of a distribution relative to a normal distribution. Features with low variances (or standard deviation) may be removed from data modeling since they are expected to represent a relatively homogeneous sample. Examination of higher order moments can provide more information about the existence of groups in a dataset. The higher order moments may be used in different ways. For example, data with high kurtosis in combination with high (positive or negative) skewness of the data may be used to identify groups.

At step 56, sets of characteristics are selected, either via top-down techniques such as operator selection or by techniques such as clustering and supervised machine learning algorithms to divide the cells in an image into a set of "groups" (step 58) such that the cells within a group are more similar to each other in the given feature space when compared to features of cells in other groups. Other techniques such as measurement of variance, PCA, etc., have the inherent limitation that they can only measure the existence of heterogeneity but do not divide the cells into groups. Techniques provided herein may involve visualizing the data at the level of individual cells in the image to assess the possibly groups in the image followed by an algorithmic step of identifying thresholds to delineate the cells into these distinct groups. The analysis may be provided as an output (step 60), such as a molecular heterogeneity value, a displayed output identifying the cell types, etc.

In univariate analysis, each independent feature is analyzed separately to determine if it might be useful in describing the heterogeneity in the data. For example, the distribution of cellular expression of protein A across all the cells in the image is examined separately from the distribution of cellular expression of protein B across the cells in the image. Statistics computed from the underlying distributions of these proteins will indicate whether each protein is expressed homogeneously across the entire image, or if there might be different levels of expression that are indicative of distinct groups of cells. The approach may first sort the data in some order (ascending or descending order are both equally acceptable) and examine the data for any observable inflection points. The number of significant inflection points in the data point to distinct groups within the data and threshold values for distinguishing the groups. Further groups may be found in the region of gentler inflection points that may or may not indicate distinct groups (these may hint at heterogeneity within a larger group). A similar process may be applied to multivariate data by projecting the higher dimensional data onto a line (2-D) or a plane (>=3-D) and finding inflection points in the resulting distribution of data points. The specific technique used is detecting the best number of "clusters" in a multi-dimensional dataset. The main idea is to divide the cells into varying numbers of clusters and then identifying the best "number of clusters" in a dataset based on metrics comparing within-cluster to between-cluster variation.

An advantage to using the inflection point technique (specifically in a higher dimensional mode) is that it can take external models or derived features as inputs. For example, it could take in output of PCA that have been found in a separate processing step using biomarker expression values and compare the spread of these groups in the context of morphological features. Other acceptable inputs are techniques that create cell groupings as an output such as clustering (supervised or unsupervised), data modeling techniques such as SVMs, NNs, pathway analysis, etc.

The heterogeneity observed in a tissue is reported as a diversity index that is based on two distinct components. The molecular heterogeneity is a measure of how many different types of cells are in a population of cells or in other words the overall diversity of the population of cells. Cells that belong to the same type (or exhibit a similar molecular "signature") will still differ from each other to a degree that is smaller than the difference between distinct types. In addition, the diversity may include a spatial heterogeneity, which is a measure of whether cells tend to be different from their neighbors. Spatial heterogeneity may be a measure of a distance between similar cells or clusters or, may be a measure of the overall diversity in the neighborhood of a particular cell. For example, if a cell is surrounded by similar cells (e.g., in a cluster), the spatial diversity in that area is low. If, instead, the immediate neighborhood of a particular cell is very diverse, the spatial diversity is relatively higher. The cell similarity may be assigned based on the analysis used in determining the molecular heterogeneity. That is, the techniques may use the cell types determined via univariate or multivariate analysis.

Figure 4:
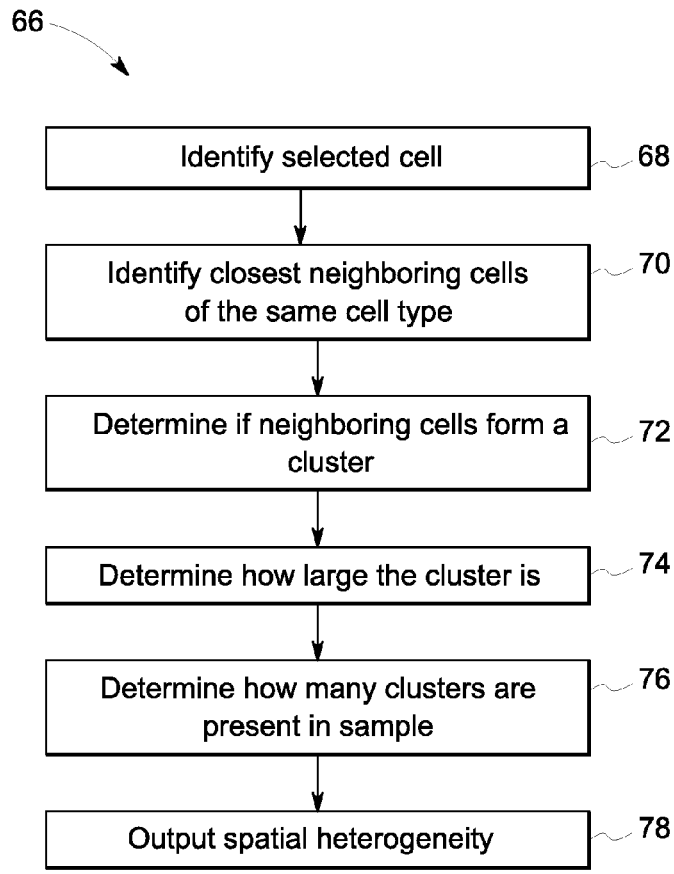
FIG. 4 is a flow diagram of a spatial heterogeneity characterization according to an embodiment of the present disclosure.

FIG. 4 is a flow diagram of one embodiment of a technique 66 of determining spatial heterogeneity by assessing the diversity of cell clusters within a sample. In the disclosed embodiment, a cell may be selected (step 68) and its closest neighboring cells of the same cell type are identified (step 70). Then, a cluster analysis is performed to determine if the neighboring cells form a cluster (step 72) and to determine the size of the cluster (step 74). In addition, an analysis may determine how many clusters are present in the sample (step 76). Based on the number, size, and distance between clusters, a spatial heterogeneity score may be determined (step 78).

Figure 5:
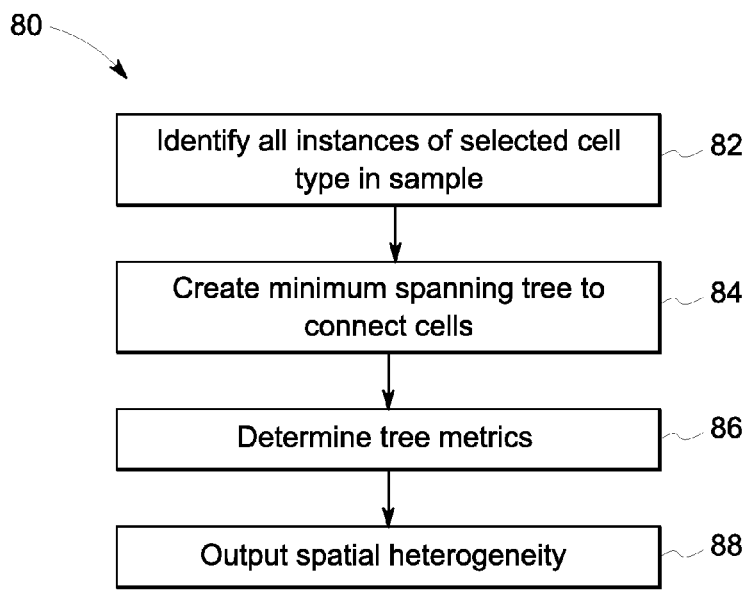
FIG. 5 is a flow diagram of a spatial heterogeneity characterization according to another embodiment of the present disclosure.

In one embodiment, shown in FIG. 5, a technique 80 for determining spatial heterogeneity involves assessing the spatial differences between cells of a given type. That is, the technique first identifies all cells in a sample (or FOV) of a particular cell type or cell group having common characteristics (step 82), such as biomarker expression, morphological characteristics, or a combination thereof. Then, the technique 80 proceeds to determining a distance between all cells of the particular type within the sample (or FOV). In one embodiment, this is accomplished by creating a minimum spanning tree (step 84), such as a Euclidean Minimum Spanning Tree (EMST) to connect the centroids of cells of a given type. For example, the EMST may contain many small line segments for tissue having low spatial heterogeneity, where the length of these line segments is approximately the same as the size of the cells themselves. These segments may be assessed to determine tree metrics (step 86) to determine the spatial heterogeneity (step 88). If sections of tissue are spatially separated into separate islands, the EMST would also contain a small number of longer line segmentations that join these islands. Alternately, for tissue having higher spatial heterogeneity, the line segments of the EMST would largely be greater than the size of the cells. This process results in a spatial heterogeneity score separately for each defined cell type.

In one embodiment, the minimal spanning trees connect cells in the different spaces. Given a connected, undirected graph, a spanning tree of that graph is a subgraph that is a tree and connects all the vertices together. A single graph can have many different spanning trees. A weight may be assigned to each edge indicating favorability (or lack thereof), and this may be used to assign a weight to a spanning tree by computing the sum of the weights of the edges in that spanning tree. A minimum spanning tree (MST) or minimum weight spanning tree is then a spanning tree with weight less than or equal to the weight of every other spanning tree. More generally, any undirected graph (not necessarily connected) has a minimum spanning forest, which is a union of minimum spanning trees for its connected components.

Figure 6:
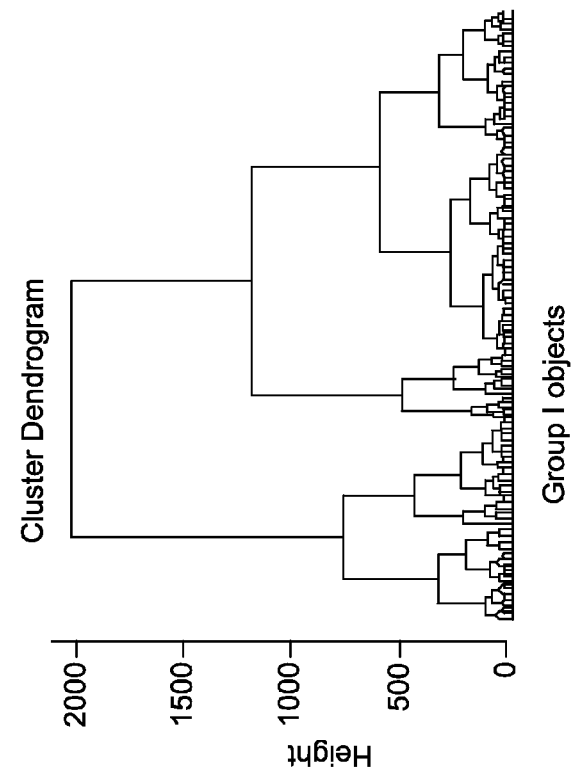
FIG. 6 is a plot of a minimum spanning tree of group object cells in a biological sample with an associated cluster dendrogram.
Figure 6:
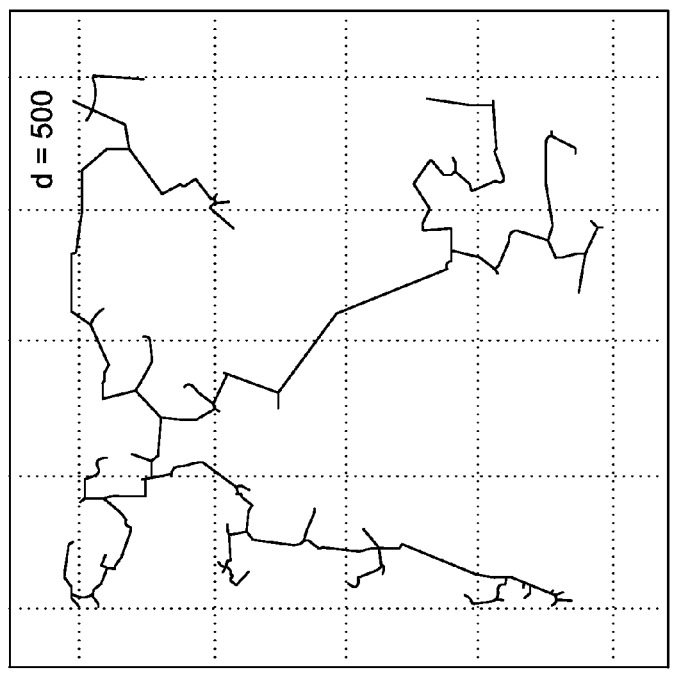
Figure 7:
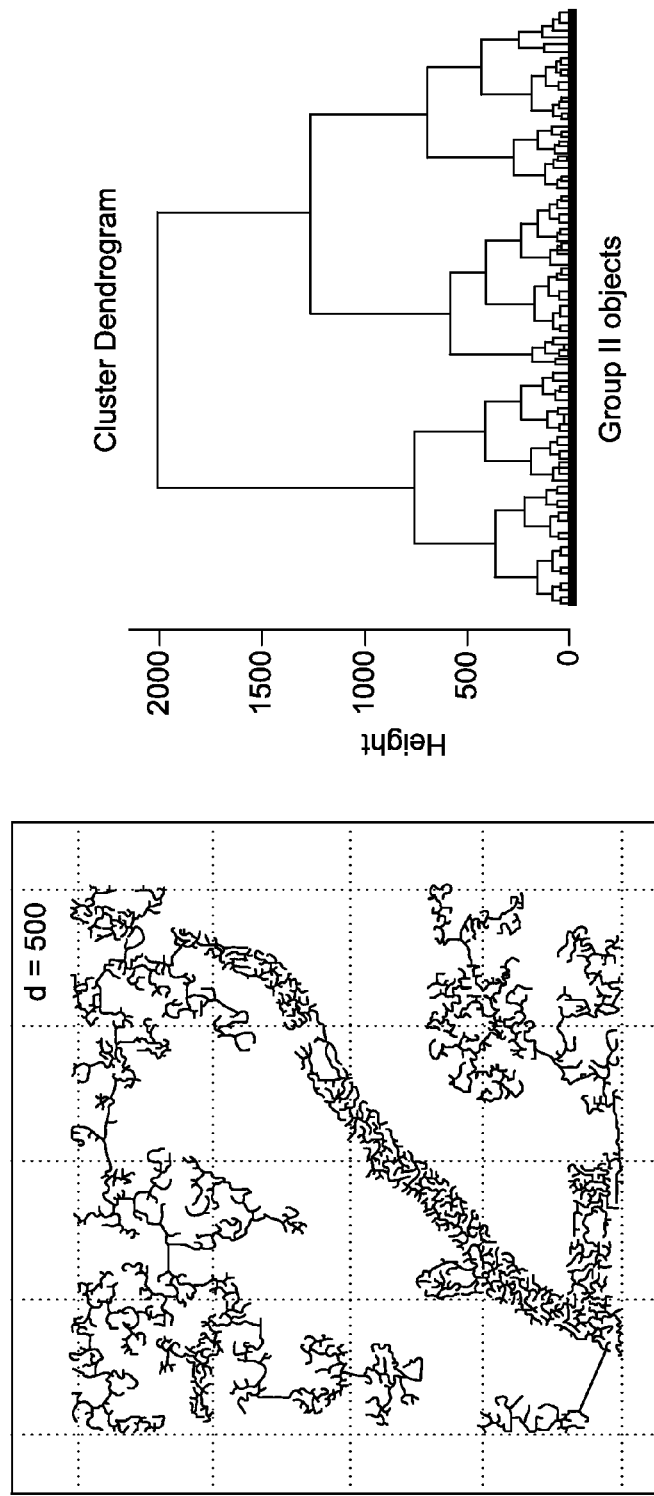
FIG. 7 is a plot of a minimum spanning tree of group object cells of a different group in the biological sample of FIG. 6 with an associated cluster dendrogram.

For assessing molecular heterogeneity, the minimal spanning trees are used to connect cells in a multi-dimensional space where each dimension may have different scales depending on the type of feature represented. For spatial heterogeneity, the space is simply a 2-dimensional Euclidean space that defines the x-y location of each cell within the image. Each minimal spanning tree may be analyzed in different ways to generate metrics describing the properties of the tree. Metrics such as "closeness" of cells, "edge-betweenness", "shortest paths", "average path length" etc. may be used to characterize the distribution of cells within the given space. For example, the metric "average path length" may be used to assess the spread of cells in the space. FIG. 6 shows an example of a minimum spanning tree representation based on the expression of protein AQP5 (aquaporin5) being greater than a predetermined threshold and the corresponding cluster dendrogram. FIG. 7 shows a minimum spanning tree representation and the corresponding cluster dendrogram of the group representative of AQP5 expression of the same sample below the threshold. The minimum spanning trees show the cells of one cluster type, which would be one cluster in the dendogram, e.g., a cluster in the dendogram would be shown by a vertical line intersecting a horizontal cut point. In one embodiment, the spanning trees in FIG. 6 and FIG. 7 could share the same dendogram. Each spanning tree would correspond to one cluster in the shared dendogram.

Figure 8:
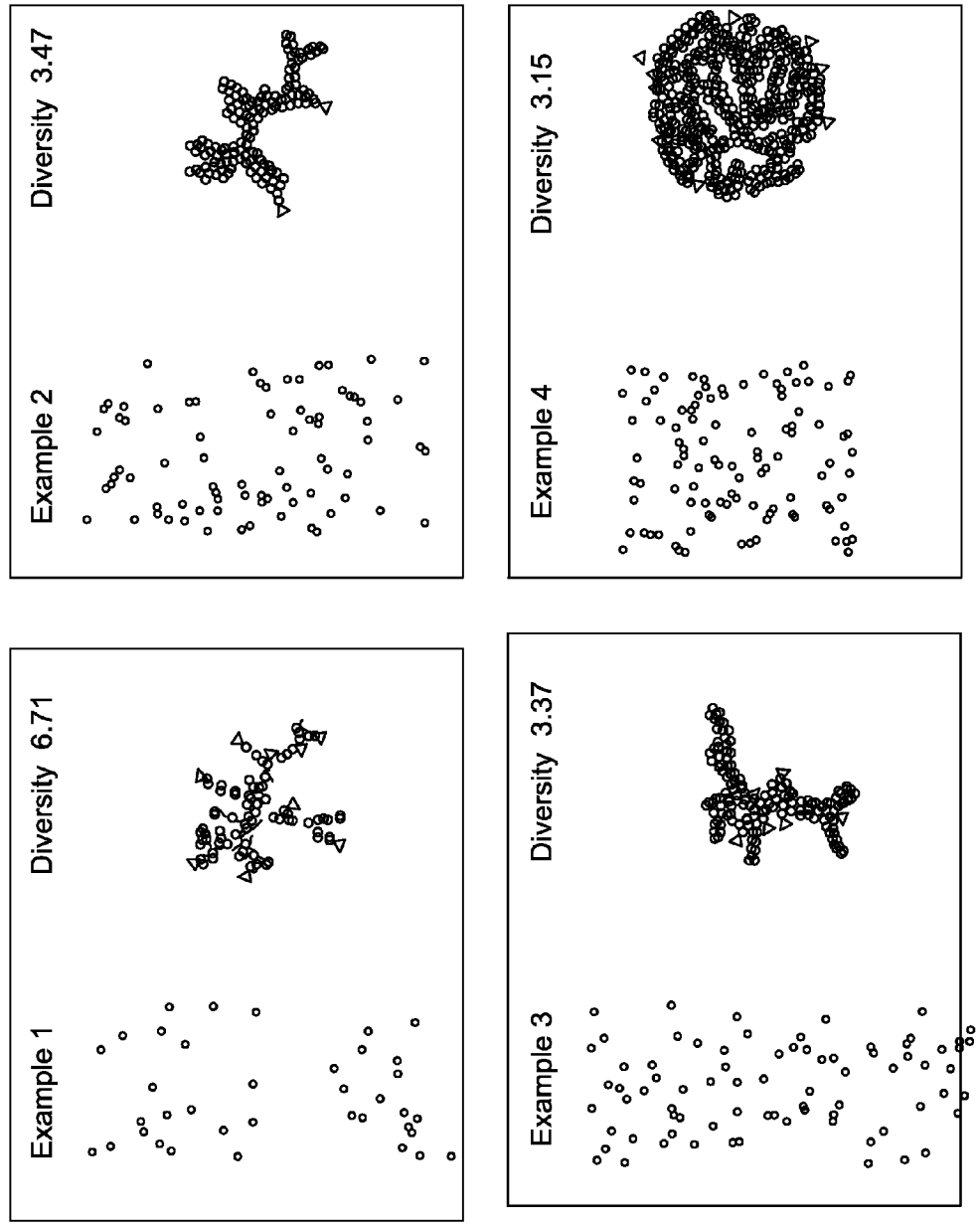
FIG. 8 shows diversity scores for different cell spatial arrangements and associated plots.

When comparing clusters, a relatively tighter spread of the cells within a cluster will translate to a lower value of the average path length, indicating close proximity between the cells in the cluster, and lower spatial heterogeneity. Cells that are further apart in a cluster are more diffuse and have higher spatial heterogeneity. FIG. 8 shows examples of how the metric "average path length" increases or decreases according to the relative spread of the data points in Euclidean space.

It may be more efficient to assess the heterogeneity in a sample within a specific context, such as heterogeneity of tissue architecture, heterogeneity of protein expression within tumor cells, or in tumor compared to normal cells, etc. Accordingly, the overall diversity index or its component heterogeneity indices may change based on the selected techniques. As an intermediate step, in certain embodiments, the technique generates a "2-D Calibration Plot" (using the two indices) to allow different interpretations of the data based on the specified context. Calibration curves may be generated by computing the indices for a variety of images that exhibit different levels of heterogeneity with regard to different types of inputs (protein expression, morphological features, tissue architecture). Each point in this plot represents the index for a single group extracted in an image. Manual ground truth data is collected for each image based on the observed heterogeneity. For a given context, it is then straightforward to draw a "Calibration Curve" that associates a level of heterogeneity to a pre-specified outcome.

Calibration plots may also be drawn using more samples from the dataset. Ground truth measurement values of heterogeneity or some outcome variable can then be used to calibrate the diversity index measurements for predicting the corresponding outcome for a patient sample. Manual ground truth measurements were collected by a biologist for the observed molecular heterogeneity in an image. The biologist used color blended images for visualization (distinct colors assigned to the individual biomarker values) and divided the image into multiple groups if multiple color groups were observed in the stroma. The image was categorized as displaying "high", "medium" or "low" heterogeneity based on the distinct colors observed. The spatial heterogeneity was similarly categorized as "high", "medium" or "low" depending on the spread of cells in each of the cell groups observed.

The measurements provided herein are divided into two separate metrics, combined in the simplest form via a calibration plot. In some cases, it might be beneficial to present the information as a single index value for an image instead of the two-metric index. The reduction of the index to a single value largely depends on the application of the index to a biological question.

For example, if it is more important to understand the characteristics of the "most heterogeneous group in the molecular feature space", the reduction step simply involves summarizing the metrics for the cell group that had the largest molecular heterogeneity value. Similarly, if the most interesting group is the one with the highest spatial spread, the reduction step involves summarizing the metric for the cell group with the highest spatial heterogeneity metric. Other options could be explored as well, for example, selecting the group with the largest scalar length in the calibration plane. This selects the group with the largest collective heterogeneity. The biological relevance of such groups will depend on the tissue and disease type.

Figure 9:
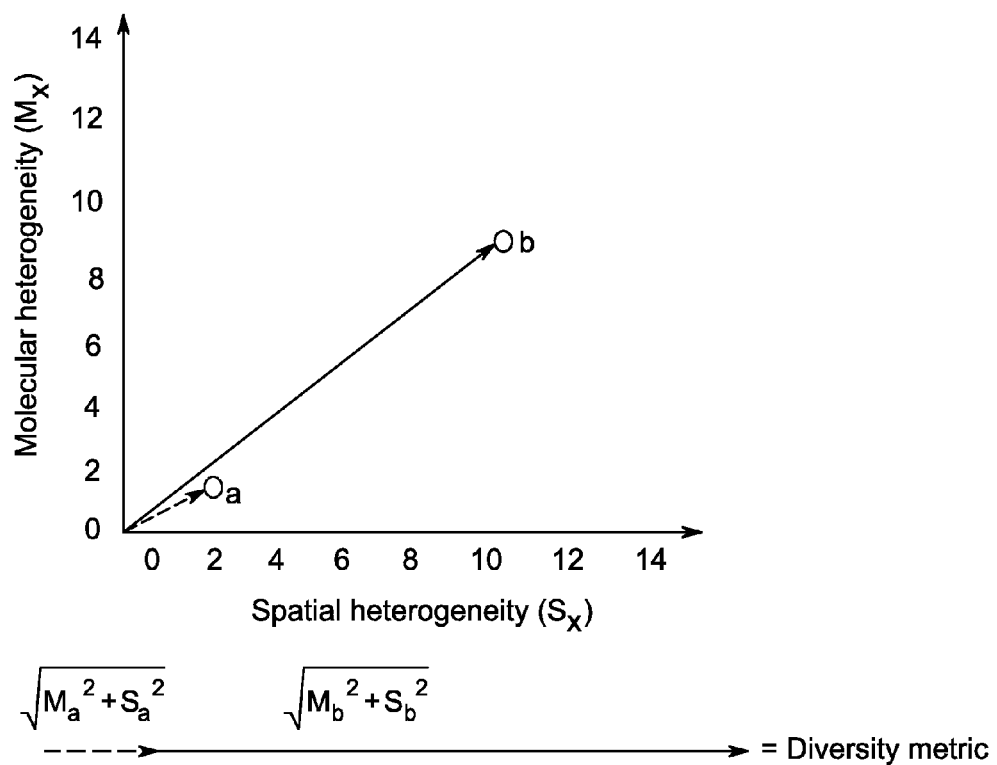
FIG. 9 shows a plot associating molecular and spatial heterogeneity.
Figure 10:
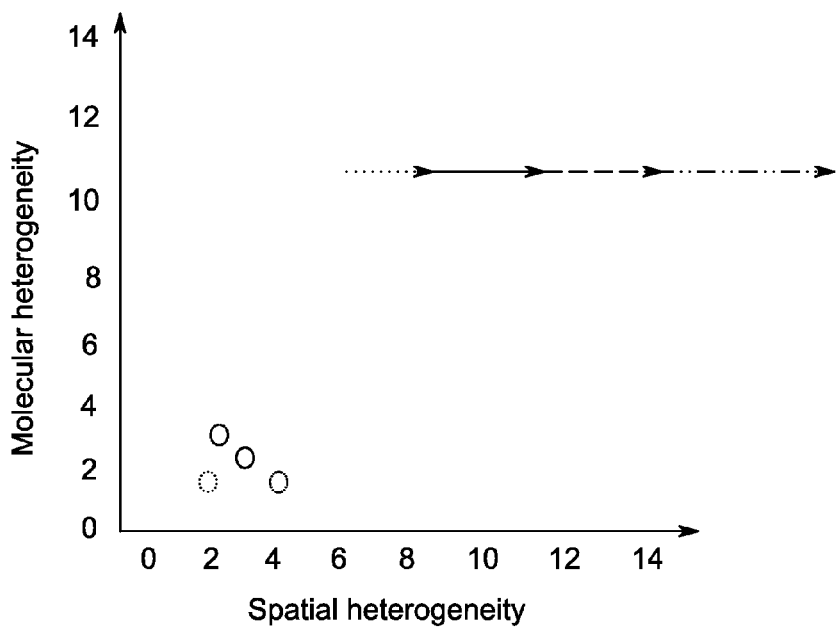
FIG. 10 shows a plot showing components of molecular and spatial heterogeneity for a low diversity case.
Figure 11:
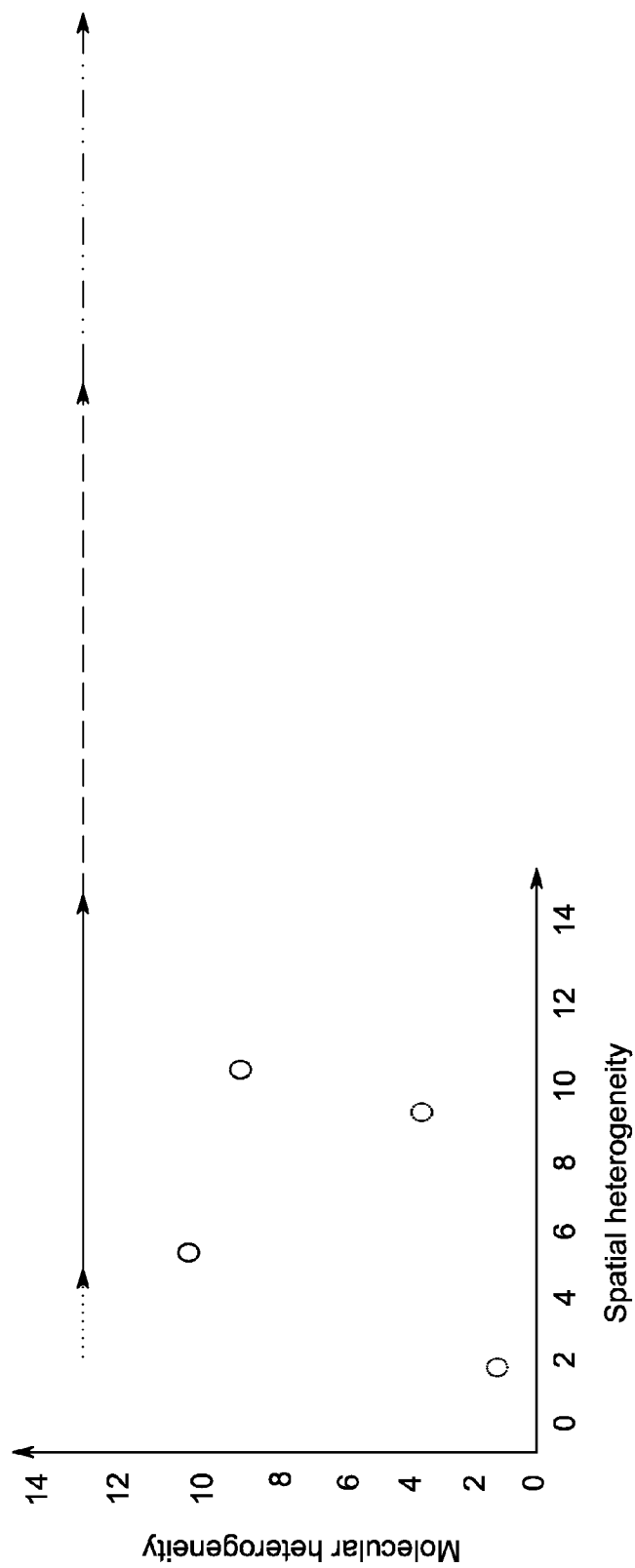
FIG. 11 shows a plot showing components of molecular and spatial heterogeneity for a high diversity case.

In FIG. 9 the metrics are reduced to a single diversity index value by taking all the extracted groups in account. Consider a vector drawn from the origin of the calibration plot (Mol. Het.=0 and Spatial Het.=0) to the calibration point for each cell group 'x' ($M_x$, $S_x$). The individual heterogeneity values are combined through scalar addition of each vector in an image, as shown in FIGS. 10-11.

When an image contains only one group, the diversity index is simply the length of the vector: a straightforward combination of the molecular and spatial heterogeneity indices. If the image contains multiple groups with low heterogeneity values (more or less homogeneous), the final metric will be higher than any of the individual values but still a relatively low value (compared to a truly heterogeneous sample). The presence of multiple groups with distinct molecular signatures is clearly represented in this higher diversity index value. If the image contains a very heterogeneous group and the rest are homogeneous, the heterogeneity values for this group will contribute the largest to the output index and the rest will contribute minimally. The presence of the other groups is accounted for in the metric but will not skew the metric. If the image contains many heterogeneous groups, the final metric will be very high, correctly indicating a very heterogeneous sample.

Figure 12A:
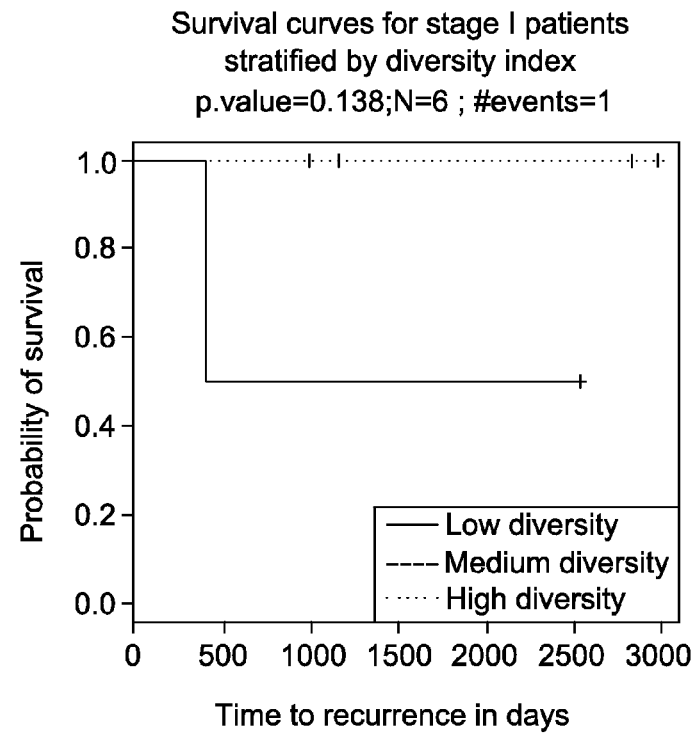
FIG. 12A shows plots of survival curves for stage I and stage II patients.
Figure 12A:
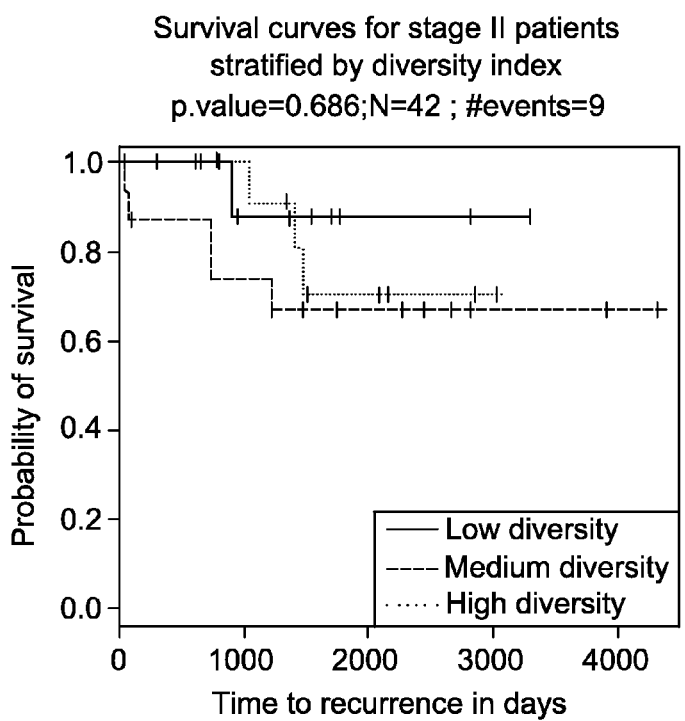
Figure 12B:
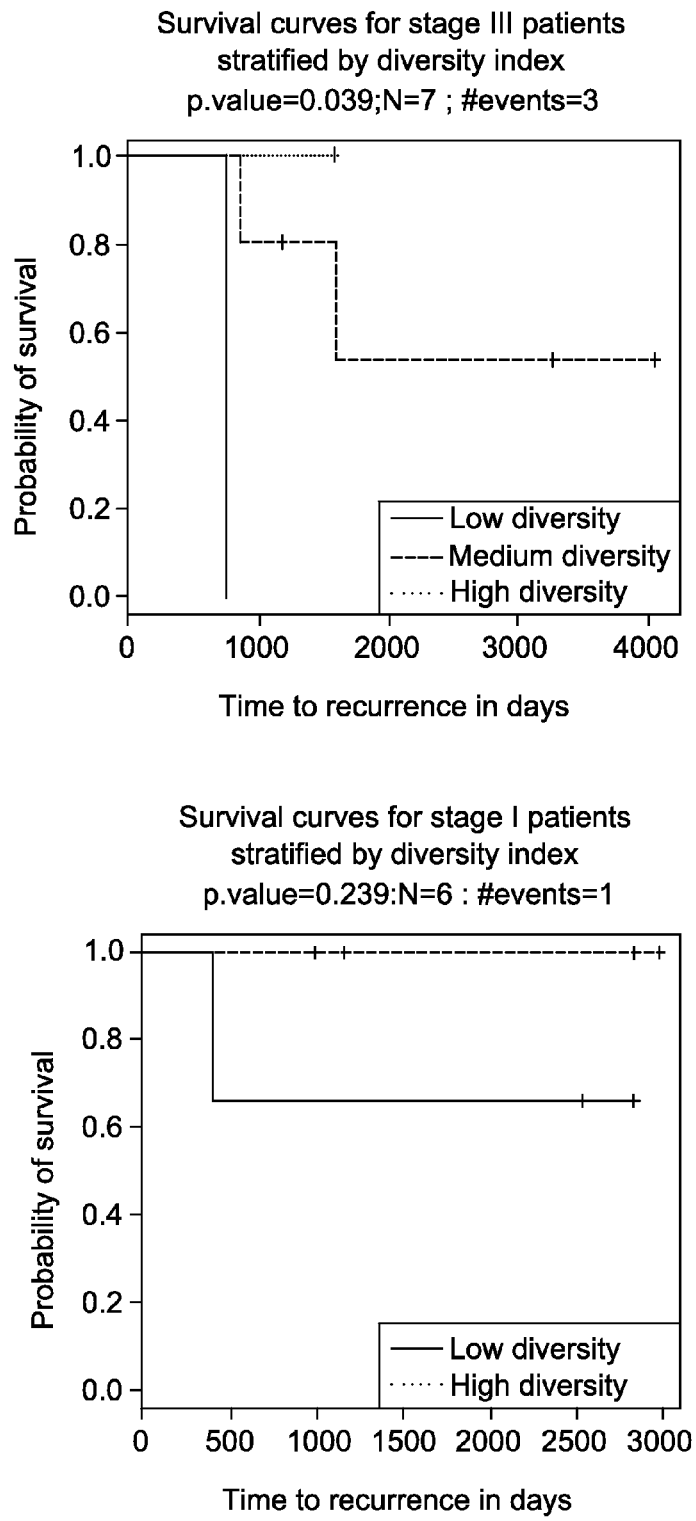
FIG. 12B shows plots of survival curves for stage III and stage I patients.
Figure 12C:
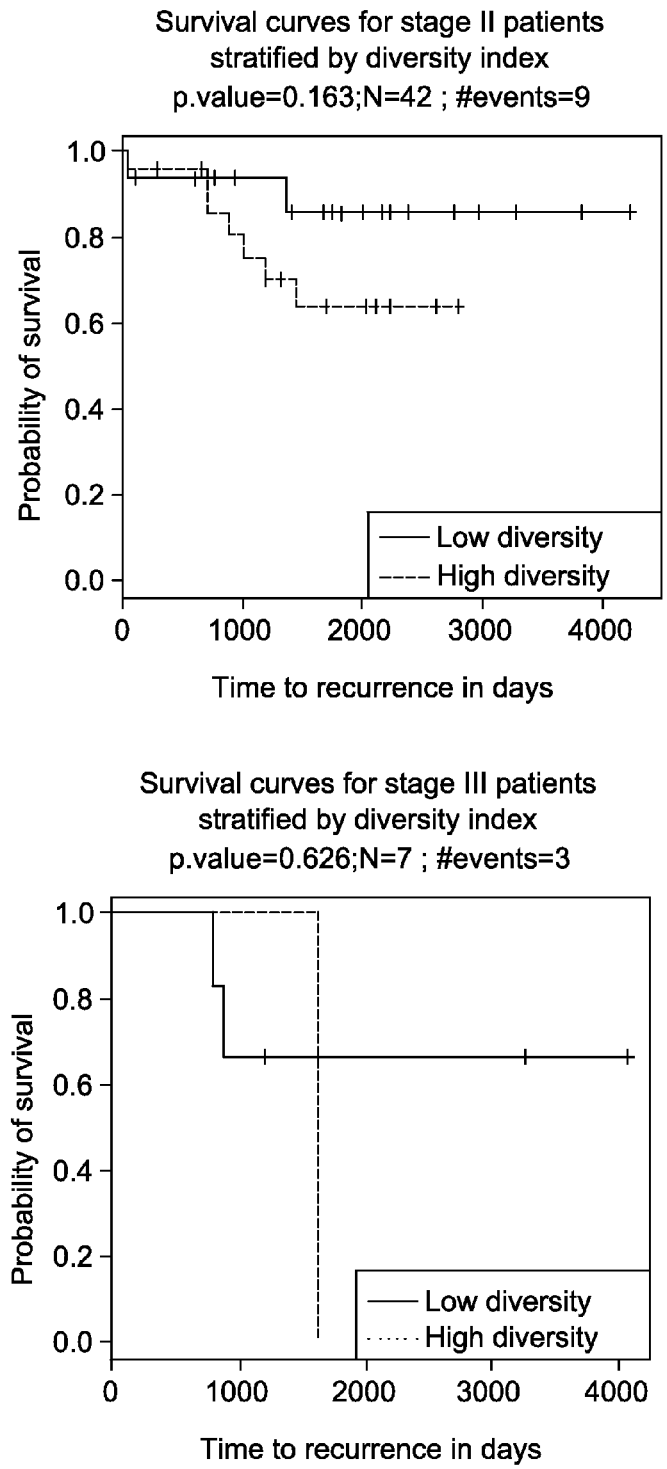
FIG. 12C shows plots of survival curves for stage II and stage III patients.

The diversity index may be used for patient stratification or to predict an outcome for a tissue sample, such as the tumor grade, stage or survival outcome. The diversity metric as computed herein may be used to correlate the heterogeneity observed in a tissue sample to the desired outcome. As shown in FIG. 12A-C, the metric correlates to recurrence of disease. The two-metric measure was first condensed to a single metric as described into a single diversity index. This index is a continuous valued variable and was utilized in two ways for survival analysis: The continuous valued diversity index was used in a Cox proportional hazards model to determine if the observed heterogeneity in an image could be indicative of disease recurrence. The Cox PH model was generated by using ⅔ of the dataset as a training set and the model used to predict on the remaining ⅓ samples as a test (not shown here as the fit was not acceptable). These results indicate that the diversity index measuring heterogeneity across all stages of tumor is unable to clearly predict disease recurrence. Tumor heterogeneity might be expected to vary differently at the different stages of tumor. The continuous valued diversity index was split into two (high and low heterogeneity; FIGS. 12B and 12C) and three levels (high, medium and low heterogeneity; FIGS. 12A and 12B) to plot survival curves and to determine if a simpler representation of diversity could be an indicator of survival or recurrence of disease. FIG. 12A shows plots of survival curves for stage I and stage II patients. FIG. 12B shows plots of survival curves for stage III and stage I patients. FIG. 12C shows plots of survival curves for stage II and stage III patients.

EXAMPLES

Tissue samples of colorectal cancer were collected at the Clearview Cancer Institute of Huntsville Ala. and provided to GE Global Research by Clarient Inc. This tissue microarray (TMA) imaging cohort consisted of 747 paraffin-embedded patient tumor samples distributed across three slides. These samples underwent multiplexed fluorescence microscopy (MxIF) and the results and experimental details have been reported previously (Gerdes 2013). Clinical measures for each patient were provided including the histological tumor grade, cancer stage, patient sex, age, chemo treatment (yes/no), and follow-up monitoring of 10 years (medium of 4.1 years). A total of 692 samples passed MxIF image quality assessments. Table 1 presents a breakdown of samples by histological grade and cancer stage. Table 2 presents the number of patients with or without a reoccurrence event during follow-up, broken down by cancer stage and treatment protocol. For each tissue sample (i.e. field of view (FOV)), the MxIF images were segmented into cells and sub-cellular locations. Metrics for each cell were then computed including each cells centroid x and y location and cell area. Furthermore, cells were classified as either belonging to an epithelial or stromal region within each FOV

TABLE 1

|  | Grade 1 | Grade 2 | Grade 3 | Totals |
|---|---|---|---|---|
| Stage 1 | 46 (25%) | 128 (69%) | 11 (6%) | 185 |
| Stage 2 | 37 (14%) | 208 (79%) | 19 (7%) | 264 |
| State 3 | 22 (9%) | 171 (70%) | 50 (21%) | 243 |
| Totals | 105 (15%) | 507 (73%) | 80 (12%) | 692 |

TABLE 2

| Follow-up Reoccurrence Event [No/Yes (%)] | No Chemo | Chemo Treated | Totals |
|---|---|---|---|
| Stage 1 | 140/8 (5.4%) | 31/6 (16.2%) | 171/14 (7.6%) |
| Stage 2 | 122/16 (11.6%) | 97/29 (23%) | 219/45 (17%) |
| State 3 | 42/20 (32.3%) | 112/69 (38.1%) | 154/89 (36.6%) |
| Totals | 304/44 (12.6%) | 240/104 (30.2%) | 544/148 (21.4%) |

Thresholds were computed for the protein Immunofluorescence (IF) measures in order to classify a specific measure as being high, medium, or low relative to all measures within the study. This three state (high, medium, low) threshold model requires the assignment of two threshold values to bin measures into high, medium, and low representing the top ⅓, middle ⅓, bottom ⅓ of the sorted measures for each IF measure at each location (e.g. whole cell, cytosol, nuclear, membrane). There are alternatives to a three state threshold model such as a binary model (high, low) or threshold models with greater resolution (i.e. 4, 5, or more bin states). The thresholds were generated for each segmented whole cell and the segmented sub-cellular regions of cytosol, nuclear, and membrane regions. The thresholds were computed using the mean marker value within the segmented region. The alternative of using the median marker value within a segmented region could also be used. Thresholds were computed using 692 tissue image fields of view (FOV) that passed image quality assessments. Initially only 56 FOV's were used to build the thresholds and the performance of the approach held up. However, thresholds may be built using a training set to perform predictions on FOV's that were not used to build the thresholds.

The Shannon diversity index was used to characterize the heterogeneity of the MxIF tissue images. The Shannon diversity index can characterize how many different states are observed in a tissue and how evenly the cells of the tissues are distributed among those observed states. This entropy metric can range in values from 0 (no entropy) to a positive number representing greater entropy. Because a tissue has a limited number of cells, the maximum value the entropy metric is reached when every cell is expressing its own unique state. This maximum entropy value is equal to the natural log (ln) of the number of cells in the tissue. Therefore, in a field of view (FOV) that includes 2,000 cells, the FOV's entropy metric can range between 0 (no entropy) and 7.6 (maximum entropy).

$$\text{Entropy} = -\Sigma_i^N p_i \ln(p_i) \quad \text{(Equation 1)}$$

where

N: number of unique observed states $p_i$: frequency of occurrence of observed state i ln: natural logarithm A heterogeneity metric may be computed by dividing the entropy by the natural log of the number of unique observed states. Doing so provides a metric that characterizes the degree to which the cells are distributed between the observed states. The heterogeneity metric ranges from 0 (no heterogeneity) to 1 (maximum heterogeneity).

$$\text{Heterogeneity} = \frac{\text{Entropy}}{\ln(N)} \quad \text{(Equation 2)}$$

The diversity of a tissue may be characterized by the entropy and heterogeneity metrics both from a molecular and spatial context. A tissues molecular state diversity is represented by the Molecular Entropy and Molecular Heterogeneity metrics as computed using equation 1 and 2 respectively. These metrics do not include the spatial configuration, orientation and relationships of the cells within the tissue.

The spatial diversity of a sample may be computed after first selecting or constructing the algorithm to define the spatial context. For example, one could group cells expressing a specific state into spatially connected cell families. Algorithmically, this may be accomplished by first identifying all cells that belong to state "c". For the set of "c-state" cells, they are grouped into families by their relative x-y coordinate location to each other. Those that are first neighbors (i.e. touching cells) are considered members of the same spatial family. For a family of cells defined by this spatial context, it is possible to step from one cell to another eventually reaching all cells within the family while always being contained by only stepping between first neighbors (i.e. touching cells). FIG. 13 illustrates this example using a 7 by 7 grid to represent an image field of view of 49 cells. The grid contains 12 cells that are expressing the "c-state". Some of the "c-state" cells are touching each other and these may be grouped into c-state spatially defined cell families. This is illustrated in FIG. 13 using grey scale coloring (or hatch patterning) of the grid cells to represent the family size. For example, c-state single cell families that contain only one cell in which the single cell is not first neighbors to any other cell expressing the c-state are filled with double-line hatching.

TABLE 3

| Cell State | Number Observed Cells | $p_i$ | $p_i \ln(p_i)$ |
|---|---|---|---|
| A | 4 | 4/49 = 0.082 | −0.2045 |
| B | 6 | 6/49 = 0.122 | −0.2572 |
| C | 12 | 12/49 = 0.245 | −0.3446 |
| D | Not observed | | |
| E | 5 | 5/49 = 0.102 | −0.2329 |
| F | 11 | 11/49 = 0.224 | −0.3354 |
| G | 1 | 1/49 = 0.020 | −0.0794 |
| H | 10 | 10/49 = 0.204 | −0.3243 |

In Table 3, the number of cells=49, the number of unique observed cell states, N=7. Cell states "c", "f", "h" are the $1^{st}$, $2^{nd}$, and $3^{rd}$ most frequently observed states. The Molecular_Entropy=$-\Sigma_i^N p_i \ln(p_i)$=0.97; and the $$\text{Molecular\_Heterogeneity} = \frac{\text{Entropy}}{\ln(N)} = \frac{0.97}{\ln(7)} = 0.5.$$

The entropy metric can range from 0 for no entropy to ln(N)=ln(7)=1.95 indicating maximum molecular entropy. The heterogeneity metric can range from 0 for no heterogeneity to 1 for maximum molecular heterogeneity.

TABLE 4

| "c-state" Cell Family Size | Number Observed "c-state" Cell Families | $p_i$ | $p_i \ln(p_i)$ |
|---|---|---|---|
| 1 | 2 | 2/6 = 0.333 | −0.3662 |
| 2 | 3 | 3/6 = 0.500 | −0.3466 |
| 3 | Not observed | | |
| 4 | 1 | 1/6 = 0.167 | −0.2986 |

In Table 4, the number of "c-state" cell families=6, the number of unique observed "c-state" cell family sizes, N=3, c-state Spatial_Entropy=$-\Sigma_i^N p_i \ln(p_i)$=1.01, and $$rgw \text{ } c\text{-state Spatial\_Heterogeneity} = \frac{\text{Entropy}}{\ln(N)} = \frac{1.01}{\ln(3)} = 0.92.$$

The entropy metric can range from 0 for no entropy to ln(N)=ln(3)=1.099 indicating maximum spatial entropy. The heterogeneity metric can range from 0 for no spatial heterogeneity to 1 for maximum c-state spatial heterogeneity. Other metrics that were computed include ratios such as the Spatial_Entropy divided by the Molecular_Entropy and the Spatial_Heterogeneity divided by the Molecular_Heterogeneity. These were discovered to provide additional information since molecular entropy can rise while spatial entropy decreases in some diseased tissues.

Using the segmented tissue images it is possible to represent the edge of each cell by a set of pixel points. When deciding if two cells are spatially first neighbors (i.e. touching cells), the edge pixel points from the two cells may be compared seeking for the condition in which the distance between an edge pixel point from one cell is within one pixel distance of an edge pixel point from another cell. This comparison of polygon points is considered the exact method. Alternatively, one could implement an approximate but computationally more efficient approach (2× faster). The Euclidean distance between each cell's centroid x and y location could be computed and normalized by the sum of the approximate radius for the two cells. If this normalized distance is equal to or less than some critical distance then the cells are considered to be first neighbors. For example:
 dr=(area_cell_1/3.14)^0.5+(area_cell_2/3.14)^0.5
 dx=centroid_x_cell_1−centroid_x_cell_2
 dy=centroid_y_cell_2−centroid_y_cell_2
 normalizedSqrDistance=(dx*dx+dy*dy)/(dr*dr)
 if
 (normalizedSqrDistance<=CRIT_SQR_DISTANCE_FACTOR)
  firstNeighbors=true
  else
  firstNeighbors=false Pathway state diversity metrics may be computed by first selecting one or more pathway maps. These pathway maps may be obtained from public knowledge bases or derived from independent data sources. Gene sets in which the genes are linked as identified from experimental data (e.g. co-expression data) or from a gene ontology system (e.g. Gene Ontology Consortium) may also be used. In a general example, the data may be assessed by determining the quality of staining for each field of view (FOV) and removing those that do not pass. Then, a method may perform cell segmentation on each FOV and generate biomarker measures (mean value) for each cell and sub-cellular location (cytosol, nuclear, membrane). The method may compute the centroid x and y location and cell area for each cell in each FOV and classify each cell of each FOV as belonging to either an epithelial or stromal region. Biomarker thresholds may be generated (e.g. 2, 3, 4, or 5 state model) on the data at the study, slide, and FOV level. For example, in a 3 state threshold model, the technique may generate 2 threshold values to bin measures into high, medium, and low representing the top ⅓, middle ⅓, bottom ⅓ of the sorted measures for each biomarker and for each location (e.g. whole cell, cytosol, nuclear, membrane). Then, the pathway state for each cell may be determined, e.g., by assigning a state value to each pathway map node.

Figure 14:
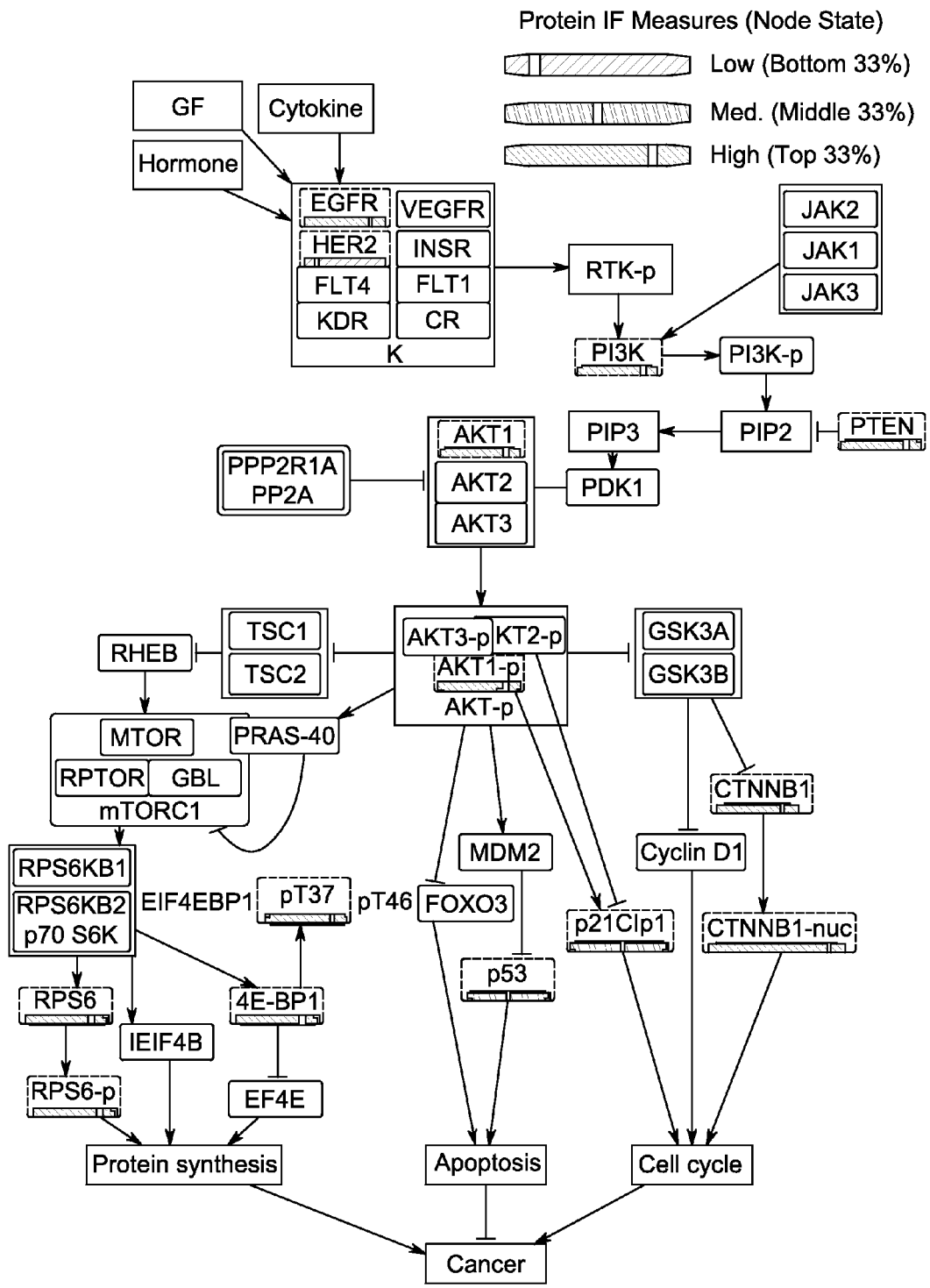
FIG. 14 is an example of a pathway state map.

FIG. 14 presents one example pathway map that is focused around the AKT pathway. A pathway map consists of nodes that can represent both an entity (e.g. protein, RNA, small molecule, nucleotide sequence), potentially in particular entity state (e.g. phosphorylation, methylation, glycosylation, etc.) and a spatial context (e.g. cell cytosol, nucleus, membrane, etc.). The edges that connect the nodes represent biological processes such as reactions, inhibition, activation, membership, etc.

A pathway map state may be assigned to each individual cell by utilizing the cell's individual protein immunofluorescence (IF) measures to define the pathway state. The process to define a cell's pathway state starts by first ordering the measurable nodes of the pathway map by some reproducible methodology. The easiest is to use the node identification (ID) values, ordered alphabetically. Since the node ID values are stored electronically as part of the pathway map, they provide a reproducible way to define the ordering of the pathway nodes. With the measureable nodes of the pathway map ordered, they are each assigned a node state value using the cell's IF measure for the corresponding nodes. For a 3 state threshold model, the pathway map node will be assigned as low, medium, or high (e.g. numerically represented as 0, 1, 2) depending upon the cell's protein IF measure for that node. The state of the entire pathway for a cell is represented by an integer value that represents the unique state of each node in the pathway. A pathway state with up to 40 measureable nodes may be represented by a 64 bit integer using a ternary digit, or trit. Alternatively, it can be encoded as a string of numerical characters. The maximum number of possible pathway map states may be very large. For example the pathway map presented in FIG. 14 has 13 nodes that are measurable. Each node state could theoretically be low, medium, or high. Therefore the maximum number of possible pathway states is $3^{13}$=1,594,323. This number is rather large since for a typical FOV there are only about 2,000 cells.

The number of observed pathway states in "normal" tissue may be significantly less than in "cancer" tissue and significantly less than the theoretical maximum number of possible pathway states. For example, if a pathway has 14 nodes, each node state can be low, medium, or high, then the maximum number of possible pathway states is $3^{14}$=4,782,969. In reality, only 100 pathway states will be observed in "normal" regulated tissue. In cancer tissue, the number of observed pathway states may increase by 2 to 8 times producing 200 to 800 observed pathway states. This increase arises due to genetic mutations that impact regulation mechanisms impacting the individual pathway nodes. Accordingly, in certain embodiments, the present techniques use pathway states to assess the diversity of a tissue sample.

One advantage of using pathway maps provides mechanistic insight into what specific pathway states are potentially influencing therapy responses within specific subtypes, cancer stages, and tumor grade. Unlike classical k-mean and hierarchical clustering and principal component analysis, the technique of using pathway states provides mechanistic insights and understanding of what pathway states are not being observed (absent in data set) in addition to those observed (present in the data set).

The output from the pathway-based heterogeneity algorithm can provide an additional set of independent parameters for down-stream multivariate statistical analysis.

Molecular heterogeneity of single cell protein expression may be indicative of specific pathways and protein-gene set states based on the hallmarks of cancer correlate with re-occurrence in colorectal cancer. The hallmarks of cancer being: self-sufficiency in growth signals; insensitivity to antigrowth signal; tissue invasion and metastasis; unlimited proliferation potential; sustained angiogenesis; evading apoptosis; deregulated metabolism; genomic instability; tumor promoting inflammation; and avoiding immune destruction. The diversity metrics and specific states for each pathway or gene set can be correlated with outcome (e.g. cancer re-occurrence). This correlation can then be used to sort the set of pathways and gene sets to identify which is most important to the outcome for a particular cancer stage, grade, and therapy.

Figure 15:
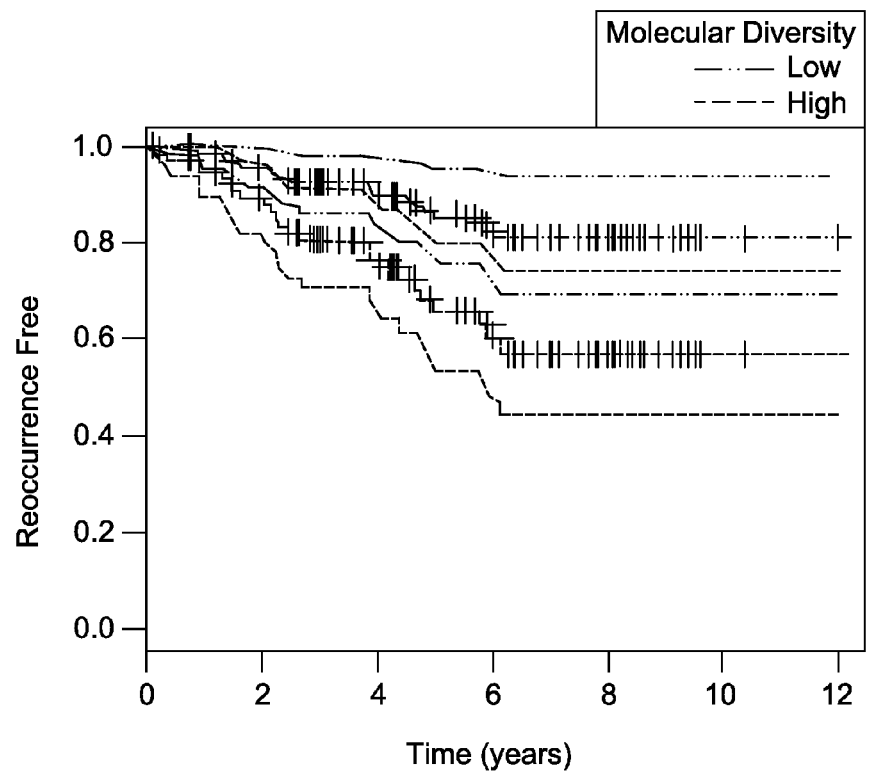
FIG. 15 shows the molecular heterogeneity of the Tumor Promoting Inflammation hallmark and its correlation with reoccurrence in Stage II CRC subjects who received chemotherapy.
Figure 15:
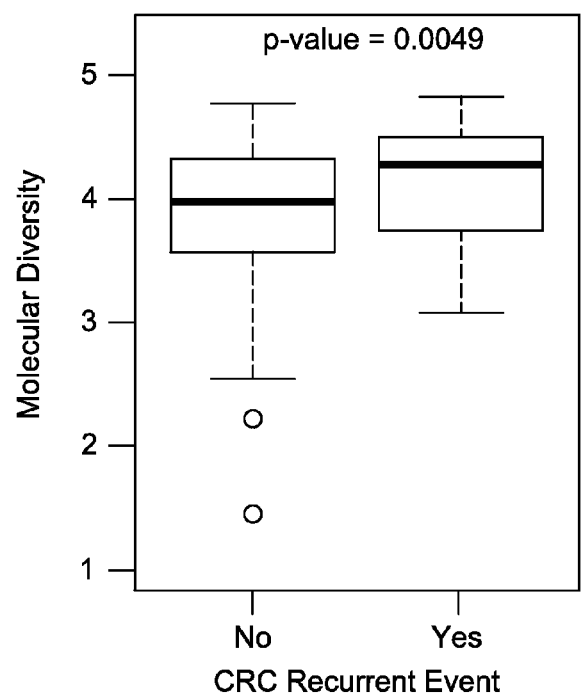

FIG. 15 illustrates just one example showing the molecular heterogeneity of the Tumor Promoting Inflammation hallmark and its correlation with reoccurrence in Stage II CRC subjects (N=102) who received chemotherapy. The single cell expression levels of four proteins Caspase-3 cleaved, Glut-1, MAPKAPK2 (pT334), Cox2 were used to compute the state of each cell. The Shannon diversity index was then used to compute the diversity or heterogeneity index. The Shannon diversity index can characterize how many different cell or pathway states are observed in a tissue (i.e. molecular context) and how evenly the cells of the tissues are distributed among those observed states (i.e. spatial context).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining heterogeneity of cell populations in a biological sample comprising:
   receiving image data of a biological sample comprising a plurality of cells, wherein the image data is representative of expression of a plurality of biomarkers;
   segmenting the plurality of cells into individual cells in the biological sample based on the image data;
   quantitating cell features of the individual cells in the biological sample based on the image data;
   generating a plurality of cell types for the individual cells, wherein each respective cell type is based on a set of cell characteristics, wherein the cell characteristics comprise a common set of biomarker expression levels, cell features, or a combination thereof;
   assigning the individual cells to only one of the generated cell types;
   determining a molecular heterogeneity value of the biological sample based on the assigning;
   determining a spatial heterogeneity value of the biological sample based at least on one individual cell assigned to an individual cell type and a physical distance to other cells of the same cell type or cell type heterogeneity within a predetermined physical distance of the at least one individual cell; and
   determining a heterogeneity metric based on the molecular heterogeneity value and the spatial heterogeneity value.

2. The method of claim 1, wherein determining the spatial heterogeneity value comprises generating a minimum spanning tree based on the image data.

3. The method of claim 1, wherein determining the spatial heterogeneity value comprises:
   identifying the individual cell type of interest from the plurality of cells;
   selecting an individual cell assigned to the individual cell type;
   selecting a plurality of neighboring cells in the biological sample within the predetermined physical distance from the individual cell and determining if any of the neighboring cells are the same cell type; and
   creating a cluster based on the neighboring cells.

4. The method of claim 3, comprising determining the total number of clusters in the biological sample.

5. The method of claim 1, wherein the set of cell characteristics comprises a range of biomarker expression levels, a range of a quantitated cell features, or a combination thereof.

6. The method of claim 1, wherein determining the spatial heterogeneity value comprises determining a spatial heterogeneity of each of the generated cell types.

7. The method of claim 1, comprising using the heterogeneity metric for gene set enrichment analysis.

8. The method of claim 1, comprising using the heterogeneity metric to assess a stage of a cancer cell type of the biological sample.

9. A method for determining heterogeneity of cell populations in a biological sample comprising:
receiving image data from a biological sample;
selecting a plurality of biomarker characteristics of interest, wherein the biomarker characteristics comprise one or more predetermined expression levels of respective biomarkers;
determining a number of cell types in the biological sample based on the plurality of biomarker characteristics;
assigning individual cells in the biological sample to only one of the determined cell types;
calculating a physical distance across the biological sample between a plurality of cells assigned to the same cell type; and
outputting a heterogeneity metric based on the number of cell types and the calculated physical distance.

10. The method of claim 9, wherein calculating the physical distance between the plurality of cells comprises generating a minimum spanning tree based on the image data.

11. The method of claim 9, wherein determining the heterogeneity metric comprises:
identifying a cell type of interest from the plurality of cells;
selecting a single cell of the cell type;
selecting a plurality of neighboring cells in the biological sample within a predetermined physical distance from the single cell and determining if any of the neighboring cells are the same cell type; and
creating a cluster based on the neighboring cells.

12. The method of claim 11, comprising determining the total number of clusters in the biological sample.

13. The method of claim 9, wherein the plurality of biomarker characteristics of interest comprises a low biomarker expression level within a first range and a high biomarker expression level within a second range, wherein the second range is non-overlapping with the first range.

14. The method of claim 13, comprising determining the cell types based on a common set of expression levels for subset of the plurality of biomarkers.

15. The method of claim 9, comprising segmenting the biological sample into the individual cells based on the image data representative of expression of segmenting biomarkers.

16. An image acquisition device configured to acquire image data from a biological sample comprising:
a memory storing instructions that, when executed, results in:
receiving image data of a biological sample comprising a plurality of cells, wherein the image data is representative of expression of a plurality of biomarkers;
segmenting the plurality of cells into individual cells in the biological sample based on the image data;
quantitating morphological features of the individual cells in the image data;
generating a plurality of cells types for the individual cells, wherein each respective cell type is based on a set of cell characteristics, wherein the cell characteristics comprise a common set of biomarker expression levels and morphological features;
assigning the individual cells to only one of the generated cell types;
determining a molecular heterogeneity value of the biological sample based on the assigning;
determining a spatial heterogeneity of the biological sample based at least on one individual cell assigned to an individual cell type and a physical distance to other cells of the same cell type or a cell type heterogeneity within a predetermined physical distance of the at least one individual cell; and
a processor configured to execute the instructions stored in the memory; and
a graphical user interface configured to display at least a portion of the image data and the heterogeneity metric output.

17. The device of claim 16, wherein the spatial heterogeneity value is based on a minimum spanning tree.

18. The device of claim 16, wherein the morphological features comprise one or more of a cell size range, a cell shape metric, a cytoplasmic size range, or a nuclear size range.

19. The device of claim 16, wherein generating the plurality of cell types is based on one or more user inputs of biomarkers of interest.

20. The device of claim 16, wherein determining a spatial heterogeneity value of the biological sample comprises determining a cell retention level of the biological sample, wherein the spatial heterogeneity value is only determined when the cell retention level is above a predetermined threshold.

21. The device of claim 16, wherein the determining the heterogeneity metric output comprises plotting the molecular heterogeneity value and the spatial heterogeneity value on a calibration curve.

22. The device of claim 16, wherein the determining the heterogeneity metric output comprises determining the spatial heterogeneity value of the individual cell type having the highest heterogeneity.

* * * * *